US008709996B2

(12) United States Patent
Leane et al.

(10) Patent No.: US 8,709,996 B2
(45) Date of Patent: Apr. 29, 2014

(54) PHARMACEUTICAL TREATMENT PROCESS USING CHITOSAN OR DERIVATIVE THEREOF

(75) Inventors: Michael Leane, Merseyside (GB); Alan Smith, Nottingham (GB); Lisbeth Illum, Nottingham (GB)

(73) Assignee: Archimedes Development Limited, Nottingham (GB)

( * ) Notice: Subject to any disclaimer, the term of this patent is extended or adjusted under 35 U.S.C. 154(b) by 288 days.

(21) Appl. No.: 12/766,487

(22) Filed: Apr. 23, 2010

(65) Prior Publication Data

US 2010/0203119 A1    Aug. 12, 2010

Related U.S. Application Data

(60) Division of application No. 11/271,403, filed on Nov. 12, 2005, now abandoned, which is a continuation of application No. PCT/GB2004/002057, filed on May 13, 2004.

(30) Foreign Application Priority Data

May 13, 2003  (GB) ................................. 0310919.6

(51) Int. Cl.
| | | |
|---|---|---|
| *A61K 31/722* | (2006.01) | |
| *A61K 38/28* | (2006.01) | |
| *A61K 38/16* | (2006.01) | |
| *A61K 33/42* | (2006.01) | |
| *A61K 38/12* | (2006.01) | |
| *A61K 38/21* | (2006.01) | |
| *A61K 38/20* | (2006.01) | |
| *A61K 9/48* | (2006.01) | |

(52) U.S. Cl.
USPC ........... 514/1.1; 424/400; 424/601; 424/85.2; 424/85.4; 514/4.8; 514/45; 514/55

(58) Field of Classification Search
None
See application file for complete search history.

(56) References Cited

U.S. PATENT DOCUMENTS

| | | | | |
|---|---|---|---|---|
| 5,320,853 | A * | 6/1994 | Noda et al. ..................... | 424/472 |
| 5,468,503 | A * | 11/1995 | Yamada et al. ................ | 424/461 |
| 5,744,166 | A * | 4/1998 | Illum ............................. | 424/501 |
| 6,030,953 | A | 2/2000 | Bailly et al. | |
| 6,190,694 | B1 * | 2/2001 | Mizushima et al. ........... | 424/451 |
| 6,248,363 | B1 * | 6/2001 | Patel et al. ..................... | 424/497 |
| 6,323,189 | B1 * | 11/2001 | Hardinge-Lyme .............. | 514/55 |
| 6,368,629 | B1 * | 4/2002 | Watanabe et al. ............. | 424/482 |
| 2001/0007673 | A1 | 7/2001 | Goldenberg et al. | |
| 2001/0024658 | A1 | 9/2001 | Chen et al. | |

FOREIGN PATENT DOCUMENTS

| | | |
|---|---|---|
| WO | 9009780 A1 | 9/1990 |
| WO | 9901498 A1 | 1/1999 |
| WO | WO 00/61111 | * 10/2000 |

OTHER PUBLICATIONS

Dodane, V., and Vinod D. Vilivalam, "Pharmaceutical Applications of Chitosan", Sep. 1998, Pharmaceutical Science & Technology Today, vol. 1, Issue 6, pp. 246-253.*
Zhang, Z., and Miqin Zhang, "Calcium phosphate/chitosan composite scaffolds for controlled in vitro antibiotic drug release", Aug. 2002, Journal of Biomedical Materials Research, vol. 62, Issue 3, pp. 378-386.*
Office Action Issued Mar. 28, 2007 in EP Application No. 04732650.9, related to U.S. Appl. No. 11/271,403.
Communication Under Rule 71(3) EPC, dated Jan. 14, 2008, in European Application No. 04732650.9, with Amended Application as Allowed.
Martindale, "The Complete Drug Reference," Pharmaceutical Press, 33rd Edition, Royal Pharmaceutical Society (front page and publication details only), 2002.
USP26/NF21, "The United States Pharmacopeia," 2002, pp. 2155.
Washington, "Particle Size Analysis in Pharmaceutics and Other Industries, Theory and Practice," Ellis Horwood Limited, Chapter 3, 1992, pp. 61-78.
Inoyatov et al., "Preparation and Evaluation of a Prolonged Release Pentoxifylline Tablet with Chitosan," Pharm. Ind., vol. 60, 1998, pp. 472-475.
Thanou et al., "Intestinal Absorption of Octreotide Using Trimethyl Chitosan Chloride: Studies in Pigs," Pharmaceutical Research, vol. 18, No. 6, 2001, pp. 823-828.
Luessen et al., "Mucoadhesive polymers in peroral peptide drug delivery. IV. Polycarbophil and chitosan are potent enhancers of peptide transport across intestinal mucosae in vitro," Journal of Controlled Release, vol. 45, No. 1, 1997, pp. 15-23.
Shu, "Novel pH-sensitive citrate cross-linked chitosan film for drug controlled release," International Journal of Pharmaceutics, vol. 212, No. 1, 2001, pp. 19-28.
Office Action issued Jun. 10, 2009 in U.S. Appl. No. 11/271,403.
Office Action issued Jan. 25, 2010 in U.S. Appl. No. 11/271,403.
International Search Report issued on Sep. 9, 2004 in International Application No. PCT/GB2004/002057.
International Preliminary Report on Patentability issued on Nov. 18, 2005 in International Application No. PCT/GB2004/002057.

* cited by examiner

*Primary Examiner* — Robert A Wax
*Assistant Examiner* — Randeep Singh
(74) *Attorney, Agent, or Firm* — Panitch Schwarze Belisario & Nadel LLP (57) ABSTRACT

The present invention provides a solid composition for oral administration comprising:
 (i) a drug compound;
 (ii) chitosan or a derivative thereof or a salt of chitosan or salt of a derivative of chitosan; and
 (iii) an organic acid.
Preferably the drug compound is a polar molecule having a molecular weight of 1 KDa or less, a peptide, a protein or a polysaccharide. The compositions of the invention provide enhance absorption of the drug compound.

21 Claims, 5 Drawing Sheets

Figure 1. Dissolution of chitosan from capsule formulations at pH 7.2 (mean. n=3)

Figure 3. Dissolution of chitosan from capsule formulations at pH 5.6 (mean, n=3)

Figure 4. Release of sodium salicylate from capsule formulations at pH 5.6 (mean, n=3)

PHARMACEUTICAL TREATMENT PROCESS USING CHITOSAN OR DERIVATIVE THEREOF

CROSS-REFERENCE TO RELATED APPLICATIONS

This application is a divisional of U.S. application Ser. No. 11/271,403, filed Nov. 12, 2005, which is a continuation of International Application No. PCT/GB2004/002057, filed May 13, 2004, which was published in the English language on Nov. 25, 2004, under International Publication No. WO 2004/100941 A1, the disclosures of which are incorporated herein by reference in their entireties.

BACKGROUND OF THE INVENTION

This invention relates to pharmaceutical compositions for oral administration comprising a drug compound, chitosan or a derivative thereof or a salt of chitosan or a salt of a derivative of chitosan and an organic acid.

The oral route is the preferred means by which drugs are administered to humans and animals due to its convenience, simplicity and acceptability to patients. Most conventional drugs are well absorbed from the intestines, usually by a process of passive absorption, although certain compounds are taken up by more specific means such as facilitated or active transport. Small polar molecules often display poor or erratic absorption when dosed orally. Polypeptide, polysaccharide and protein drugs cannot generally be given orally for reasons of hydrophilicity, high molecular weight and susceptibility to degradation by the acidic and enzymatic environment of the gastrointestinal tract. As a consequence, with few exceptions, negligible amounts of peptide and protein compounds are absorbed into the systemic circulation when administered by the oral route. The absolute oral bioavailability of such compounds (the percentage absorbed compared to the same dose given as an intravenous injection) is generally less than 1%. A notable exception is cyclosporin, which is a non-polar peptide compound with a partition coefficient (octanol/water) exceeding 1000.

There has been intense interest in developing novel delivery strategies to circumvent the obstacles to the delivery of peptide and protein drugs by the oral route. One possible strategy is to formulate the peptide/protein drug with a compound that enhances drug uptake across the intestinal mucosal wall.

One such compound is chitosan. Chitosan is a bioadhesive polymer derived from the acetylation of chitin and comprises glucosamine and N-acetyl glucosamine units.

The use of chitosan to increase transmucosal absorption of drug compounds is described in WO90/09780. Luessen et al, (J. Control. Rel., 45, 15-23, 1997) reported that chitosan glutamate, as an aqueous solution at pH 5.6, increased the transport of peptide compounds across Caco-2 cell monolayers and isolated rat intestinal loop. Thanou et al (Pharm. Res., 18, 823-828, 2001) investigated intestinal absorption of the peptide compound, octreotide, in pigs. Administration of an aqueous solution containing chitosan hydrochloride at pH 5.5 or trimethyl chitosan chloride at pH 7.4 led to substantial increases in bioavailability compared to a solution of octreotide alone.

The listing or discussion of a prior-published document in this specification should not necessarily be taken as an acknowledgement that the document is part of the state of the art or is common general knowledge.

The studies mentioned above used chitosan in the form of an aqueous solution. This has a number of disadvantages for oral peptide/protein administration. In particular, the peptide/protein will come into direct contact with gastric juice, with potentially serious consequences. The acid and enzyme (pepsin) content of gastric juice can result in significant degradation and loss of activity of the peptide/protein compound. In addition, many peptide/protein compounds do not have good long-term stability when prepared as aqueous solutions.

There is a need to provide a means for oral administration of drug compounds that are often not successfully administered by the oral route. Such drugs include small polar molecules, peptides, proteins and polysaccharides. In particular, there is a need to provide a composition containing these drug compounds in the form of a tablet or capsule which ensures good stability, provides effective oral absorption and allows for the possibility of acid-resistant coatings to be applied to protect the drug compound from the gastric environment.

The present invention provides a composition suitable for oral administration that addresses this need.

BRIEF SUMMARY OF THE INVENTION

For successful enhancement of absorption of a drug compound it is postulated that high local concentrations of the drug compound and an absorption enhancing compound are required. This in turn requires a dosage form from which the absorption enhancing compound and drug compound dissolve rapidly and simultaneously. To prepare a solid chitosan containing composition that meets these requirements represents a significant challenge.

Chitosan is a weak base (pKa 6.5) and an acidic environment is needed to convert its glucosamine units into the uncoiled and positively charged water-soluble form. At neutral and basic pH values, chitosan loses its charge and precipitates from solution, thus losing its potential bioadhesive and absorption enhancing properties. At higher pH values, where the chitosan is insoluble, rapid disintegration of tablet formulations has been reported (Inoyatov et al, Pharm. Ind., 60, 472-475, 1998). At lower pH, where chitosan is soluble, the tablets formed a gel matrix that inhibited the dissolution of the chitosan.

The pH of the human small intestine ranges from 5 at the jejunum to in excess of 7.5 in parts of the colon. Hence, there are areas of the intestine in which chitosan is soluble and areas in which it is insoluble.

If the pH is high, the chitosan will not hydrate and ionise and the solid dosage form will rapidly disintegrate. However, the chitosan will remain undissolved and thus unable to improve intestinal drug absorption.

If the pH is low, the chitosan will readily hydrate and ionise. Adjacent chitosan particles will adhere to each other with the result that the surface of the dosage form forms a hydrated gelled layer which inhibits water penetration into the core of the dosage form. As a result, the chitosan will dissolve only slowly from the surface of the dosage form.

Hence, there is a need to produce a solid pharmaceutical composition for oral administration from which dissolved chitosan and dissolved drug are rapidly and simultaneously liberated over the pH range found in the intestine so that the chitosan can act to improve the intestinal absorption of the drug compound. We have surprisingly found that this can be achieved by incorporating an organic acid into the solid pharmaceutical preparation.

By rapidly we mean that the rate of dissolution of the drug and chitosan using an in vitro test, such as described in the Examples, is such that the time between 20% and 75% of the drug or chitosan content in a tablet or capsule dissolving is preferably less than 240 minutes, more preferably less than 210 minutes and most preferably less than 180 minutes. By simultaneously, we mean that the time difference between 75% of the drug content and 75% of the chitosan content of a tablet or capsule dissolving is preferably less than 180 minutes, more preferably less than 150 minutes and most preferably less than 120 minutes.

We have found that combining a drug compound with chitosan or a derivative thereof or a salt of chitosan or a salt of a derivative of chitosan and an organic acid in a solid composition can enhance absorption of the drug in certain environments within the gastrointestinal tract of animals such as humans.

The present invention provides a solid composition for oral administration comprising:
a drug compound;
chitosan or a derivative thereof or a salt of chitosan or a salt of a derivative of chitosan; and
an organic acid.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Chitosan is a bioadhesive cationic biopolymer comprising glucosamine and N-acetyl glucosamine. By the term "chitosan" we include all derivatives of chitin, or poly-N-acetyl-D-glucosamine, including all polyglucosamines and oligomers of glucosamine materials of different molecular weights, in which the greater proportion of the N-acetyl groups have been removed through hydrolysis (deacetylation). In accordance with the present invention, the degree of deacetylation, which represents the proportion of N-acetyl groups which have been removed through deacetylation, should preferably be in the range 40-97%, more preferably in the range 60-96% and most preferably be in the range 70-95%.

The chitosan, chitosan derivative or salt used in the present invention should preferably have a molecular weight in the range 10,000 to 1,000,000 Da, more preferably in the range 15,000 to 750,000 Da and most preferably in the range 20,000 to 500,000 Da.

Salts of chitosan and derivatives of chitosan are suitable for use in the present invention. Salts with various organic and inorganic acids are suitable. Such suitable salts include, but are not limited to the nitrate, phosphate, glutamate, lactate, citrate, hydrochloride and acetate salts. Preferred salts are the hydrochloric acid and glutamic acid salts.

Chitosan derivatives are also suitable for use in this invention. Suitable chitosan derivatives include, but are not limited to, esters, ethers or other derivatives formed by bonding acyl and/or alkyl groups with the hydroxyl groups, but not the amino groups of chitosan. Examples include O-alkyl ethers of chitosan and O-acyl esters of chitosan. Modified chitosans, such as those conjugated to polyethylene glycol may be used in the present invention. Conjugates of chitosan and polyethylene glycol are described in WO99/01498.

Chitosans suitable for use in the present invention may be obtained from various sources, including Primex, Haugesund, Norway, FMC Biopolymer, Drammen, Norway; Seigagaku America Inc., MD, USA; Meron (India) Pvt, Ltd., India; Vanson Ltd, VA, USA; and AMS Biotechnology Ltd., UK. Suitable derivatives include those that are disclosed in Roberts, Chitin Chemistry, MacMillan Press Ltd., London (1992).

Particularly preferred chitosan compounds that may be mentioned include "ChitoClear®" available from Primex, Haugesund, Norway.

Salts of chitosan and salts of derivatives of chitosan tend to hydrate more readily than chitosan base when in contact with aqueous media. Thus, chitosan in the form of its free base (hereinafter referred to as "chitosan base") may preferably be used in the present invention to ensure that a gel layer does not form too rapidly as this could potentially slow down dissolution of the solid drug-containing composition.

Any suitable organic acid may be used in the present invention. Suitable organic acids include, but are not limited to, those comprising from 2 to 10 carbon atoms, preferably 3, 4, 5 or 6 carbon atoms. Suitable acids include lactic, glutamic, succinic, tartaric, citric, fumaric and propionic acid. The most preferred organic acid is succinic acid.

Preferably the organic acid is present in the compositions of the invention at least in part in the form of an agglomerate. Preferably at least 80%, more preferably at least 85% and most preferably at least 90% of the acid is present in the form of an agglomerate.

By the term "agglomerate" we mean an association of particles, for example acid particles. As used herein, the term "agglomerate" includes individual particles such as individual particles of acid engineered to a specific size, for example by a standard technique in the art such as precipitation, spray drying or crystallisation.

The compositions of the invention may contain one or more agglomerate particles. Typically a single dosage form contains several agglomerate particles.

The use of an agglomerate of the organic acid reduces the surface area:weight ratio of the acid and thus reduces the rate of acid dissolution. The skilled person will appreciate that by adjusting the degree of agglomeration it is possible to adjust the rate of acid dissolution. Typically, the level of acid agglomeration should be such that the chitosan particles in the dosage form are able to separate and disperse before becoming hydrated, thus allowing rapid disintegration of the dosage form.

The agglomerate of the organic acid may be in the form of a granule, pellet, tablet or acid particle engineered to a specific size. The granules, pellets or tablets can be produced by any suitable technique known to those skilled in the art. Suitable techniques include wet granulation, dry granulation (slugging), extrusion/spheronisation, fluid bed granulation, spray drying, spray congealing, coating onto an inert seed such as a sugar seed, compression and moulding.

As the skilled person will appreciate, in order to aid in the manufacturing process and in order to produce agglomerates with the desired pharmaceutical properties, such as hardness, friability, disintegration and dissolution, it may be necessary to include other ingredients in the acid agglomerates. Any suitable additional ingredients may be used. These include, but are not limited to diluents such as calcium phosphate, lactose, dextrose, mannitol and microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, surfactants such as sodium lauryl sulphate and polysorbates, and lubricants such as magnesium stearate and hydrogenated vegetable oil.

Optionally, the acid agglomerate may also be coated in order to modify its dissolution properties, for example to provide a short delay in dissolution to allow the chitosan component of the dosage form to disperse before coming into contact with dissolved acid. Coatings that can achieve this effect include those that are water soluble, those that are insoluble but water permeable and those that are soluble at the pH encountered in the small intestine. Coatings that are both water impermeable and insoluble at the pH encountered in the small intestine are unsuitable.

Suitable coating materials include polymers such as povidone, polyethylene glycol, hydroxypropylmethylcellulose, hydroxypropyl cellulose, hydroxyethylcellulose, methylcellulose, polyvinyl alcohol, sucrose, ethylcellulose, methacrylic acid copolymers such as Eudragits L and S (registered trademarks of Röhm Pharma, Darmstadt, Germany), ammonio methacrylate copolymers such as Eudragits RL and RS, cellulose acetate phthalate, cellulose acetate butyrate, hydroxypropylmethylcellulose phthalate and shellac. Preferred polymers are those which will be soluble in the environment of the small intestine, in particular povidone, polyethylene glycol, hydroxypropylmethylcellulose, hydroxypropyl cellulose, hydroxyethylcellulose, methylcellulose, polyvinyl alcohol, sucrose, methacrylic acid copolymers, cellulose acetate phthalate, cellulose acetate butyrate and hydroxypropylmethylcellulose phthalate.

The coating material may optionally include one or more additives, for example a plasticiser such as triacetin or a phthalate ester or polyethylene glycol, an anti-tack agent such as talc or magnesium stearate or colloidal silica, an anti-foaming agent and a colorant. Other suitable additives will be readily apparent to the person of ordinary skill in the art.

The acid agglomerate can be coated using techniques that are standard in the art. Suitable techniques include spray coating from an aqueous or organic solution, for example using a fluidised bed coater, pan coater or drum coater, dip coating, compression coating or electrostatic deposition. The thickness of coating layer will be dependent on the properties of the chosen coating material, but will typically be in the range of 1-100 µm.

The size of the acid agglomerate should be sufficiently large to provide a reduced rate of dissolution of the acid compared to non-agglomerated acid yet sufficiently small to allow the preparation of an acceptable pharmaceutical composition. For example, if the acid agglomerate is too large, problems may be encountered in producing a uniform mixture with the other components of the dosage form, especially if these other components have a much smaller particle size. The preferred average or mean particle size of the acid agglomerate, as measured by sieve analysis, is from 0.1 to 5 mm, more preferably from 0.15 to 3 mm and most preferably 0.2 to 2 mm, for example about 0.5 mm. Sieve analysis is described in "Particle size analysis in pharmaceutics and other industries. Theory and Practice", chapter 3, C. Washington, Ellis Horwood, Chichester, 1992.

The amount of acid is chosen in order to provide rapid dissolution of the chitosan present in the composition. The weight ratio of acid:chitosan (calculated on the basis of the amount of chitosan or a derivative or salt of chitosan or salt of a derivative of chitosan) in the composition of the invention is preferably in the range 10:1 to 1:1, more preferably in the range 8:1 to 1:1 and most preferably in the range 6:1 to 1:1.

The drug compound used in the present invention may be any drug compound for which improved absorption when administered by the oral route is required. Such drug compounds include small polar molecules (such as those having a molecular weight of 1 KDa or less), peptides, proteins and polysaccharides.

By the term "polar molecule" we mean molecules that have a partition coefficient between water and octanol at pH 7.4 of less than 10.

Examples of small polar molecule drug compounds include bisphosphonates such as clodronate, alendronate, etidronate, pamidronate and residronate, nucleoside analogue antiviral drugs such as aciclovir, and oligonucleotides. Examples of therapeutic peptides include octreotide, insulin, glucagon, calcitonins such as salmon calcitonin, parathyroid hormone and derivatives such as PTH 1-34, ADH (vasopressin) and analogues such as desmopressin, and GnRH agonists such as leuprolide and goserelin. Examples of therapeutic proteins include growth hormone, interferons, erythropoetin, interleukins, GM-CSF and G-CSF. Examples of therapeutic polysaccharides include heparin and low molecular weight heparins such as enoxaprin, dalteparin, reviparin and tinzaparin.

The compositions of the invention may contain more than one drug compound. In this situation it is not necessary for each drug to be a compound for which improved absorption when administered by the oral route is required.

As the person of ordinary skill in the art will appreciate, the amount of the drug compound incorporated into the compositions of the invention will depend on a number of factors such as the proposed dosing regimen and the potency of the drug. The amount of the drug compound incorporated into the compositions of the invention will typically be in the range 0.001 mg to 1000 mg.

The compositions of the invention may be produced in several different ways. The following are examples of steps that can be used in the production of the compositions of the invention.

The drug compound can be mixed with chitosan or a derivative thereof or a salt of chitosan or a salt of a derivative of chitosan and the organic acid, which may, for example, be in the form of acid agglomerates.

The drug compound can be incorporated into agglomerates with the organic acid, which are then mixed with chitosan or a derivative thereof or a salt of chitosan or a salt of a derivative of chitosan.

The drug compound can be formed into agglomerates, which are then mixed with the organic acid, which may be in the form of agglomerates, and chitosan or a derivative thereof or a salt of chitosan or a salt of a derivative of chitosan.

The drug compound can be formed into agglomerates with chitosan or a derivative thereof or a salt of chitosan or salt of a derivative of chitosan, which are then mixed with the organic acid, which may be in the form of agglomerates.

The mixtures produced using the steps described above can be subjected to standard tableting procedures or may be put into capsules.

The compositions of the invention are solid. They may be presented in the form of a compressed tablet, a moulded tablet and hard or soft shell capsules. Capsules may be made from any suitable material such as gelatin, hydroxypropylmethylcellulose or starch. The capsules may contain one or more of tablets, powder, granules or pellets.

The compositions of the invention may also contain other pharmaceutically acceptable ingredients such as, but are not limited to, diluents such as calcium phosphate, lactose, dextrose, mannitol and microcrystalline cellulose, binders such as povidone (polyvinylpyrrolidone), methylcellulose, polyethylene glycol, gelatin and acacia, disintegrants such as starch, croscarmellose and crospovidone, glidants such as colloidal silica, surfactants such as sodium lauryl sulphate and polysorbates, and lubricants such as magnesium stearate and hydrogenated vegetable oil, colorants and flavourings or other agents generally used in solid pharmaceutical preparations and well known to those skilled in the art.

The weight of the compositions of the invention when in the form of a tablet or a capsule is typically from 50 to 2000 mg. The combined amount of chitosan and acid in the tablet or capsule will typically be in the range 10 to 80% by weight of the composition (calculated on the basis of the amount of chitosan or derivative or salt of chitosan or salt of a derivative of chitosan). The remainder of the composition will comprise the drug compound and other pharmaceutically acceptable ingredients.

The compositions of the invention can be used for the oral administration of drug compounds intended for systemic action or for local action at the point at which the drug is released.

In a preferred aspect of the invention, the compositions of the invention may be coated with a material that protects the composition from the gastric contents and thus prevents the drug and chitosan or a derivative thereof or a salt of chitosan or a salt of a derivative of chitosan from being released until the dosage form reaches the target site for drug absorption, for example the intestines. Site specific delivery, for example into the intestines, is most conveniently achieved by application of a pH-sensitive coating that is insoluble at gastric pH but soluble at the pH of the target site. Such coatings are also known as enteric coatings. Examples of suitable pH-sensitive coatings include methacrylic acid copolymers and methylmethacrylate copolymers such as those of the Eudragit (registered trademark of Rohm Pharma, Darmstadt, Germany) L and S series, cellulose acetate phthalate, cellulose acetate butyrate, hydroxypropylmethylcellulose phthalate and shellac. Other suitable coatings are described in WO98/15265, for example.

The thickness of the coating layer will be dependent on the properties of the chosen coating material, but will typically be in the range 10-200 μm.

The layer of enteric coating polymer may optionally include one or more additives, for example a plasticiser such as triacetin or a phthalate ester or polyethylene glycol, an anti-tack agent such as talc or magnesium stearate or colloidal silica, an anti-foaming agent and a colorant. Other suitable additives will be readily apparent to the person of ordinary skill in the art.

The enteric coating may be applied using standard techniques such as spray coating of an organic solvent-based or water-based preparation onto the solid dosage form in a pan, drum or fluidised bed coating equipment.

The present invention also provides the use of chitosan or a derivative thereof or a salt of chitosan or a salt of a derivative of chitosan and an organic acid to enhance the absorption of a drug compound that is a polar molecule having a molecular weight of 1 KDa or less, a peptide, a protein or a polysaccharide, following oral administration of the drug.

The present invention also provides the use of chitosan or a derivative thereof or a salt of chitosan or a salt of a derivative of chitosan and an organic acid in the manufacture of a medicament for the oral administration of a drug compound that is a polar molecule having a molecular weight of 1 KDa or less, a peptide, a protein or a polysaccharide.

The present invention further provides a method of administering a drug compound that is a polar molecule having a molecular weight of 1 KDa or less, a peptide, a protein or a polysaccharide, which comprises administering a composition of the invention to the patient via the oral route.

The compositions of the invention may be used to treat/prevent diseases/conditions in mammalian patients depending upon the therapeutic agent(s) which is/are employed. For the above, non-exhaustive, lists of drugs, diseases/conditions which may be mentioned including those against which the therapeutic agent(s) in question are known to be effective, include those specifically listed for the drugs in question in Martindale "The Extra Pharmacopoeia", 33$^{rd}$ Edition, Royal Pharmaceutical Society (2002).

Compositions of the invention have the advantage that they may provide enhanced absorption of drugs that are not typically well absorbed when administered via the oral route following oral administration.

The invention is illustrated by the following non-limiting Examples.

EXAMPLES

Example 1

Preparation and Dissolution Testing of Chitosan Tablets

A powder blend was prepared by mixing together 20 grams of chitosan (ChitoClear®, Primex, Haugesund, Norway) and 80 grams of mannitol (Pearlitol SD200, Roquette, Lestrem, France). The chitosan had a degree of deacetylation of 93% and an approximate average molecular weight of 200,000 Da. The powder blend was compressed using a Manesty F3 tablet press (from Manesty, Liverpool, UK) fitted with 9 mm diameter circular tooling to produce tablets.

The dissolution of the tablets was measured in pH 7.4 HEPES buffer at 37° C. using United States Pharmacopeia Method II (USP26/NF21, United States Pharmacopeia Convention, Rockville, Md., USA, 2002) with paddles at 100 rpm. 250 ml of buffer was used in each dissolution beaker.

Samples of dissolution medium were collected at periodic intervals up to 240 minutes, filtered (0.45 μm) and measured for chitosan content using a ninhydrin assay.

To perform the chitosan assay, 10 ml of lithium acetate buffer was first prepared by dissolving 4.08 grams of lithium acetate in approximately 6 ml of water, adjusting to pH 5.2 with glacial acetic acid and making up to 10 ml with water. Ninhydrin reagent was made by adding 10 ml of the lithium acetate buffer to 0.8 g ninhydrin and 0.12 g of hydrindantin in 30 ml of DMSO. 0.5 ml of this reagent was added to 0.5 ml of dissolution sample in a glass scintillation vial. The vial was capped, briefly shaken and heated in boiling water for 30 minutes. After cooling, 15 ml of a 50:50 ethanol:water mixture was added to each vial and the contents vortex mixed for 15 seconds. The absorbance of each solution at 570 nm was measured and the concentration of chitosan in the sample calculated from a standard calibration curve.

In the dissolution test, the chitosan tablets disintegrated almost immediately. However, negligible amounts of chitosan were assayed in the dissolution medium (<5% of the chitosan present had dissolved) i.e. although chitosan had rapidly been released from the tablets, it did not dissolve.

Example 2

Preparation of Succinic Acid/Sodium Salicylate Pellets 220 grams of microcrystalline cellulose (Avicel PH101, FMC, Philadelphia, USA), 200 grams of succinic acid (Sigma) and 20 grams of sodium salicylate (Fluka, Buchs, Switzerland) were added to the bowl of a Kenwood food mixer. The mixture was blended for 3 minutes at 60 rpm. Water was added gradually while mixing to granulate the blend. When the granulate was deemed to have reached a consistency suitable for extrusion (230 ml water added), addition was stopped and mixing continued for a further 10 minutes. The material was then extruded using a Caleva Model 10 extruder (Caleva, Sturminster Newton, Dorest, UK) at 15 rpm. The diameter of the holes on the extruder was 1 mm. The extrudate was then spheronised in approximately 45 gram batches using a Caleva Model 120 spheroniser (Caleva, Sturminster Newton, Dorest, UK) for 10 minutes at setting 75 (2250 rpm). The pellets were dried overnight in an oven at 50° C. The final yield of dried pellets was 359 grams.

Example 3

Preparation of Coated Succinic Acid/Sodium Salicylate Pellets 150 ml of water was heated to approximately 80° C. 10 grams of hydroxypropyl methylcellulose (Methocel E5 LV, Colorcon, Orpington, UK) was dispersed into the hot water. The dispersion was cooled in an ice bath while stirring until a clear solution had formed. The solution was made up to 200 ml with water.

The pellets produced in Example 2 were sieved and the fraction between 0.71 and 1.00 mm collected (251 grams). 200 grams of these pellets were placed into the coating chamber of an Aeromatic STREA-1 fluidised bed coater (bottom spray) (Niro Aeromatic, Bubendorf, Switzerland). The Methocel solution was applied to the pellets at a coating temperature of 60° C. and application rate of 1.5 grams/minute. 175 ml of coating solution was applied giving a theoretical HPMC content in the final pellets of 4.4% w/w.

Example 4

Capsules Containing Chitosan, Succinic Acid Powder and Sodium Salicylate Powder 3.125 grams of chitosan, 6.25 g of succinic acid and 0.625 g of sodium salicylate were weighed and transferred into a polythene bag. The powders were blended together by agitation of the bag and its contents. A 320 mg sample of blend was weighed into each of 3 size 0 hard gelatin capsules (Capsugel, Basel, Switzerland).

Example 5

Capsules Containing Chitosan and Uncoated Succinic Acid/Sodium Salicylate Pellets 7.8125 grams of chitosan, 7.8125 grams of mannitol and 34.375 grams of uncoated succinic acid/sodium salicylate pellets described in Example 2 were weighed and transferred into a polythene bag. The ingredients were blended together by agitation of the bag and its contents. A 640 mg sample of blend was weighed into each of 3 size 0 hard gelatin capsules.

Example 6

Capsules Containing Chitosan And Coated Succinic Acid/Sodium Salicylate Pellets 7.583 grams of chitosan, 7.583 grams of mannitol and 33.834 grams of coated succinic acid/sodium salicylate pellets described in Example 3 were weighed and transferred into a polythene bag. The ingredients were blended together by agitation of the bag and its contents. A 659 mg sample of blend was weighed into each of 3 size 0 hard gelatin capsules.

Example 7

Dissolution of Chitosan/Sodium Salicylate/Succinic Acid Formulations

The dissolution of the formulations was evaluated as described in Example 1. In addition to chitosan, the samples of dissolution medium were also analysed for sodium salicylate content by measuring UV absorbance at 297 nm and referring this to a calibration curve (sodium salicylate in pH 7.4 HEPES buffer over a concentration range of 0.1 to 1 mg/ml). Furthermore, dissolution testing was also performed in pH 5.6 acetate buffer.

Figure 1:
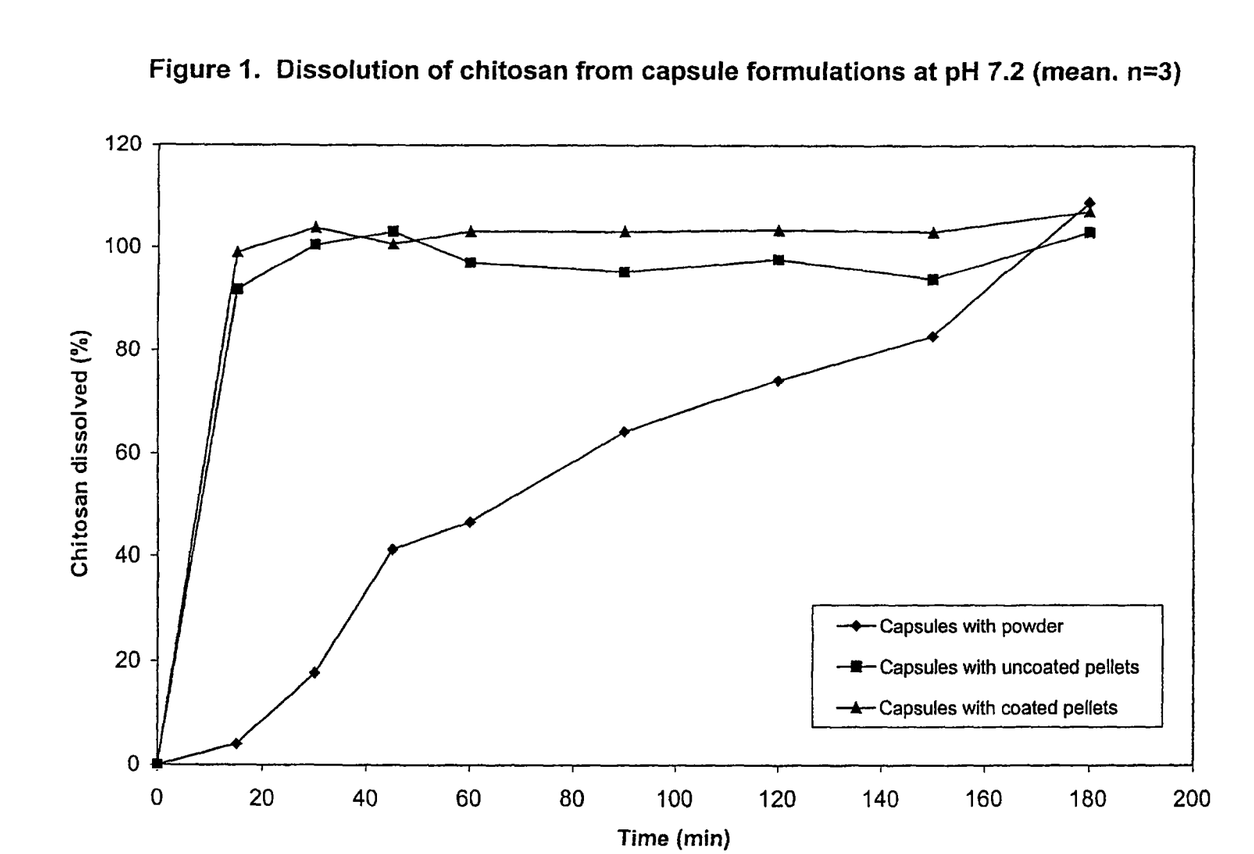
FIG. 1 shows the dissolution of chitosan from capsule formulations at pH 7.2 with time.
Figure 2:
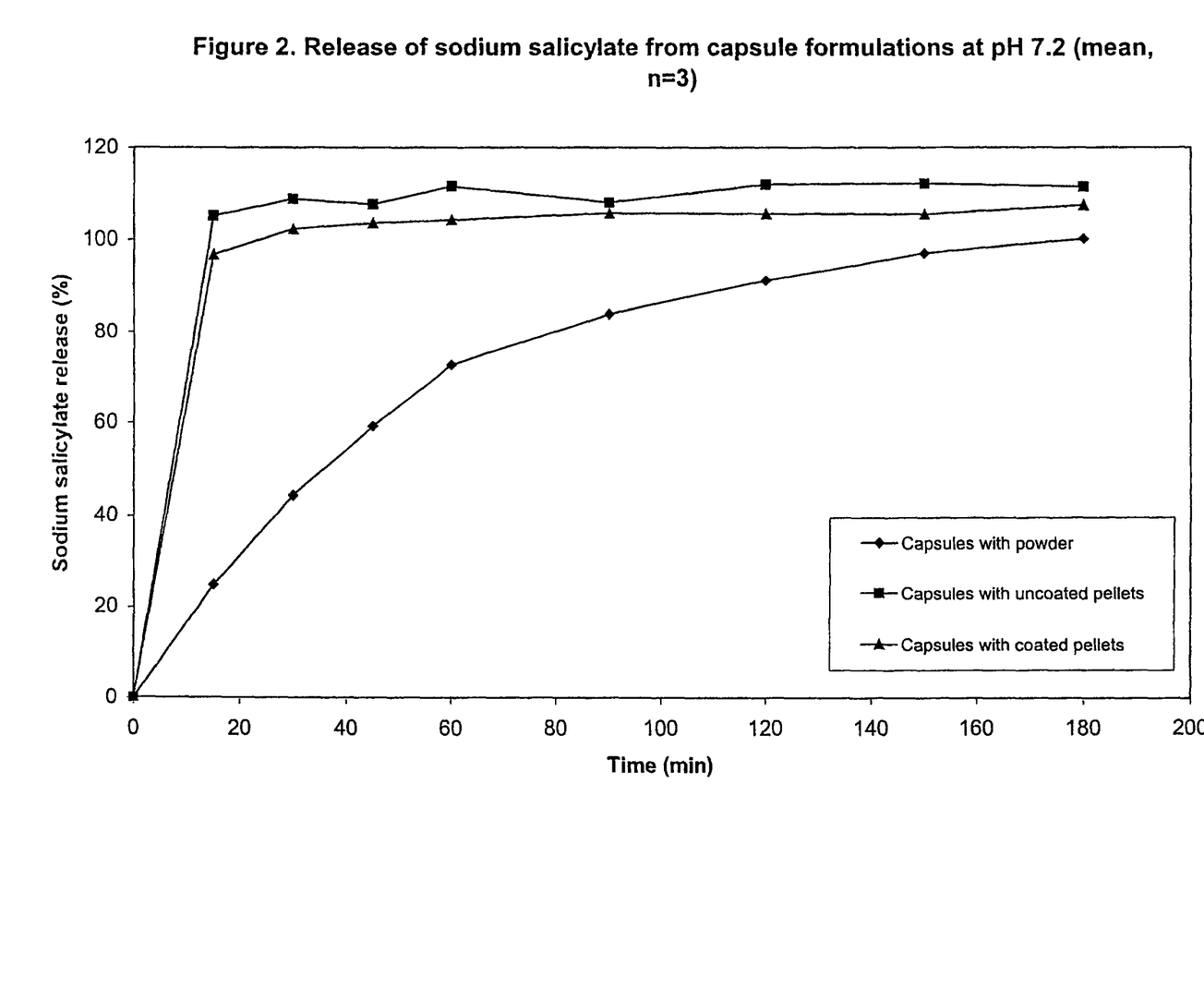
FIG. 2 shows the release of sodium salicylate from capsule formulations at pH 7.2 with time.
Figure 3:
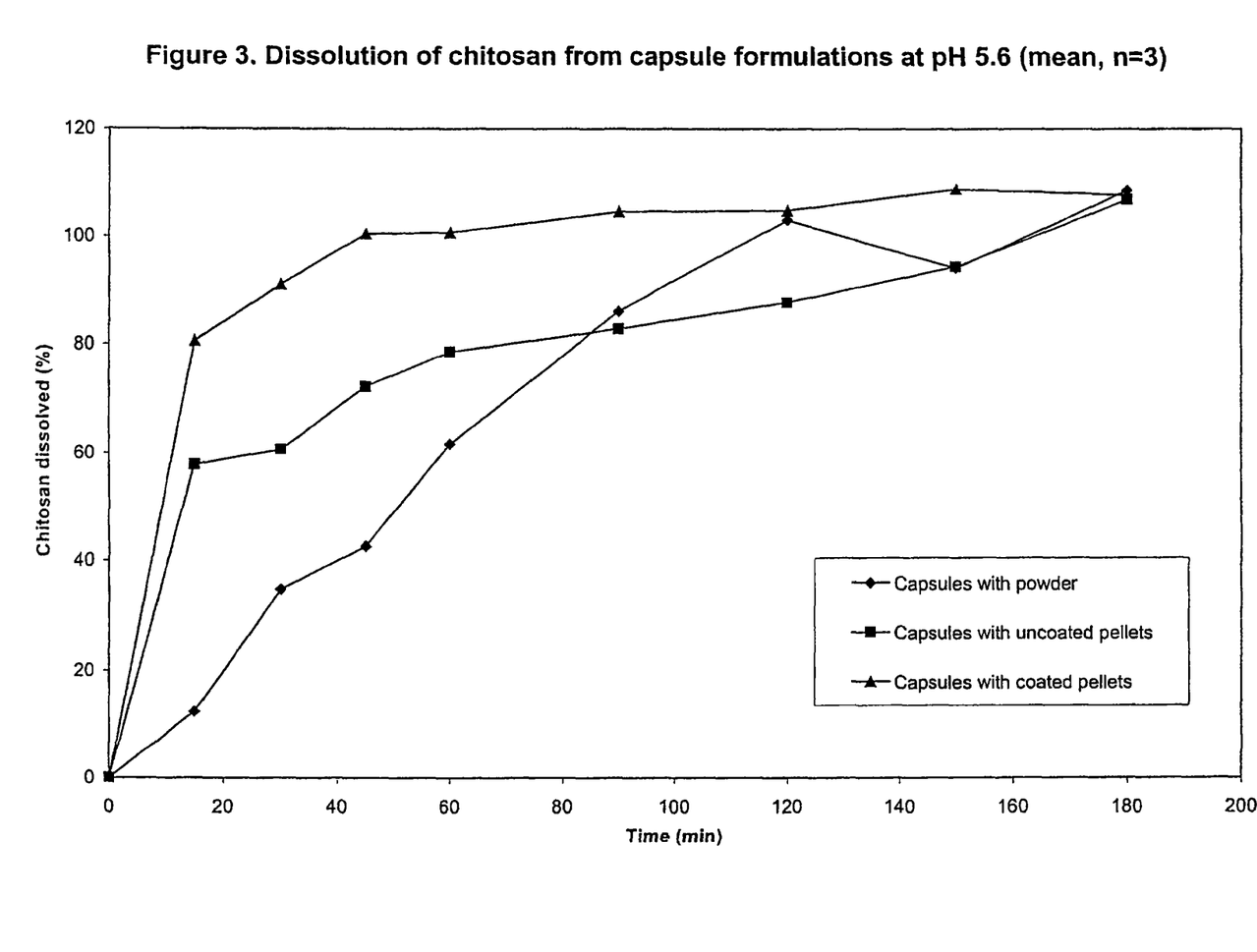
FIG. 3 shows the dissolution of chitosan from capsule formulations at pH 5.6 with time.
Figure 4:
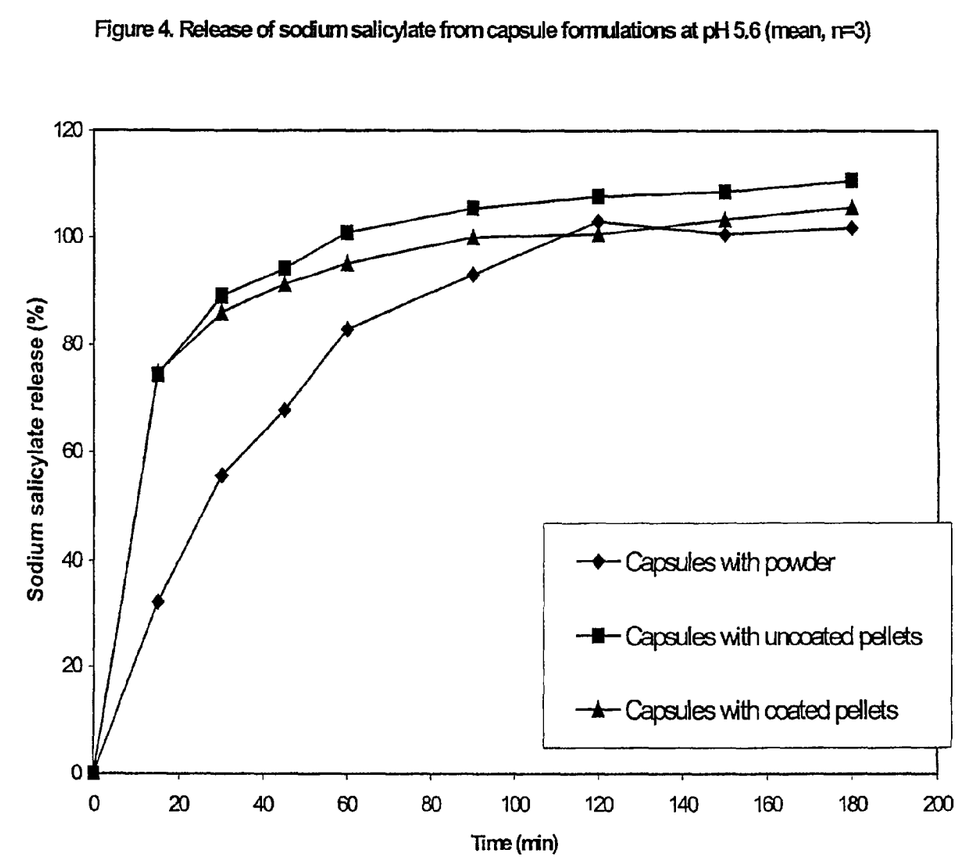
FIG. 4 shows the release of sodium salicylate from capsule formulations at pH 5.6 with time.

Dissolution data are provided in FIG. 1 (chitosan, pH 7.2), FIG. 2 (sodium salicylate, pH 7.2), FIG. 3 (chitosan, pH 5.6) and FIG. 4 (sodium salicylate, pH 5.6).

FIGS. 1 and 2 illustrate rapid dissolution of both chitosan and model drug compound (sodium salicylate) from capsules in which the acid was incorporated as uncoated and coated pellets (Examples 5 and 6 respectively). In contrast, both chitosan and drug dissolution were slow when formulated as a capsule comprising acid in the form of a powder (Example 4).

A similar pattern of dissolution was seen at pH 5.6 (FIGS. 3 and 4).

Example 8

Tablets Comprising Coated Succinic Acid/Sodium Salicylate Pellets, Chitosan and Mannitol Contained Within Capsules 2.388 grams of chitosan, 10.932 grams of coated pellets produced in Example 3 and 6.68 g of mannitol were weighed and transferred into a polythene bag. The ingredients were blended together by agitation of the bag and its contents. A Manesty F3 tablet press was fitted 6 mm round normal concave punches. Magnesium stearate (Merck Chemicals, Poole, UK) was rubbed onto the punches by hand to provide lubrication. Tablets were compressed from the blend to a target weight of 140 mg and a target hardness of 4-8 kp. Six tablets were placed in a size 0 hard gelatin capsule. Dissolution was tested as described in Example 1, with 250 ml of pH 5.6 or pH 7.2 buffer as test medium. Three capsules were tested in each dissolution beaker and testing was performed in triplicate. Chitosan concentrations were measured using the ninhydrin assay described in Example 1. Sodium salicylate concentrations were measured by UV absorbance at 297 nm.

Figure 5:
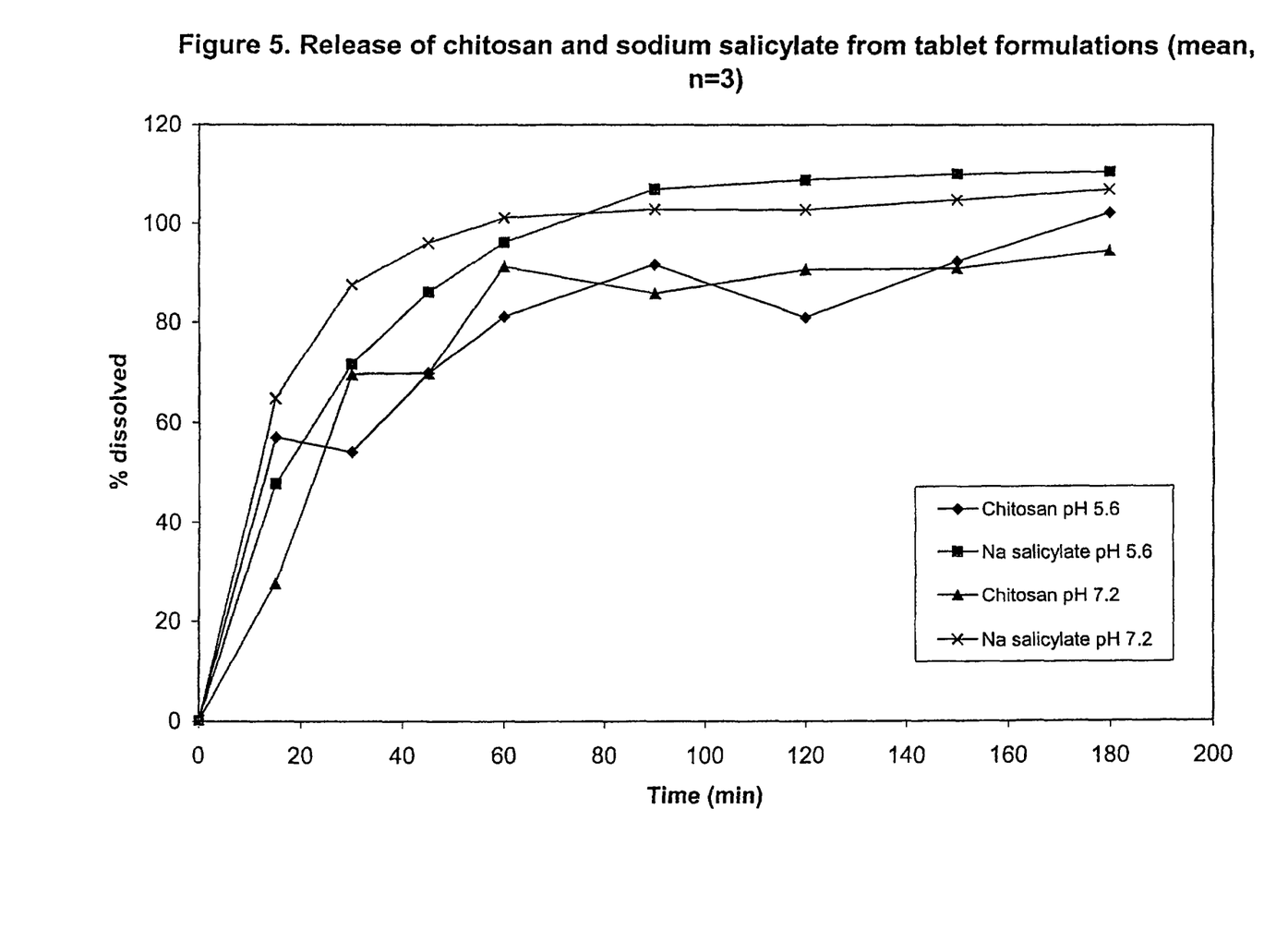
FIG. 5 shows the dissolution of chitosan and the release of sodium salicylate from tablet formulation within capsules at pH 7.2 and pH 5.6 with time.

There was rapid and simultaneous release of drug and chitosan at both pH 5.6 and pH 7.2, as shown in FIG. 5.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A process for enhancing absorption of a drug compound by a mammalian patient to which the drug compound is orally administered, wherein the process comprises orally administering to the patient a solid composition comprising a solid mixture comprising the drug compound that is a polar molecule having a molecular weight of 1 KDa or less, a peptide, a protein or a polysaccharide, and chitosan or a derivative thereof or a salt of chitosan or a salt of a derivative of chitosan, and an organic acid, wherein at least a part of the acid is in the form of an agglomerate, and wherein the acid and the chitosan or a derivative thereof or a salt of chitosan or a salt of a derivative of chitosan are present in a weight ratio of from 10:1 to 1:1, whereby absorption of the drug compound is enhanced within the gastrointestinal tract of the mammalian patient.

2. A process according to claim 1, wherein the acid is lactic, glutamic, succinic, tartaric, citric, fumaric or propionic acid.

3. A process according to claim 2, wherein the acid is succinic acid.

4. A process according to claim 1, wherein the acid agglomerate is in the form of a granule, a pellet, a tablet or an acid particle engineered to a specific size.

5. A process according to claim 1, wherein the acid agglomerate is coated with a material which modifies its dissolution properties.

6. A process according to claim 1, wherein chitosan is present in the form of chitosan base.

7. A process according to claim 1, wherein the drug compound is a bisphosphonate, a nucleoside analogue antiviral drug, or an oligonucleotide.

8. A process according to claim 7, wherein the bisphosphonate is clodronate, alendronate, etidronate, pamidronate or residronate.

9. A process according to claim 7, wherein the nucleoside analogue antiviral drug is aciclovir.

10. A process according to claim 1, wherein the peptide is octreotide, insulin, glucagon, a calcitonin, parathyroid hormone or a derivative thereof, ADH (vasopressin) or an analogue thereof or a GnRH agonist.

11. A process according to claim 1, wherein the protein is a growth hormone, an interferon, erythropoetin, an interleukin, GM-CSF or G-CSF.

12. A process according to claim 1, wherein the polysaccharide is heparin or a low molecular weight heparin.

13. A process according to claim 1, wherein the acid and the chitosan or a derivative thereof or a salt of chitosan or a salt of a derivative of chitosan are present in a weight ratio of from 6:1 to 1:1.

14. A process according to claim 1, wherein the composition is coated with a material that prevents the drug compound and chitosan or a derivative thereof or a salt of chitosan or a salt of a derivative of chitosan from being released, after administration, until the composition reaches the target site of drug absorption.

15. A process according to claim 1, wherein the composition is in the form of a compressed tablet, a moulded tablet, a hard shell capsule or a soft shell capsule.

16. A process according to claim 1, wherein at least 80% of the acid is present in the form of an agglomerate.

17. A process according to claim 16, wherein at least 85% of the acid is present in the form of an agglomerate.

18. A process according to claim 17, wherein at least 90% of the acid is present in the form of an agglomerate.

19. A process according to claim 1, wherein the average particle size of the acid agglomerate, as measured by sieve analysis, is from 0.1 mm to 5 mm.

20. A process according to claim 19, wherein the average particle size of the acid agglomerate, as measured by sieve analysis, is from 0.15 mm to 3 mm.

21. A process according to claim 20, wherein the average particle size of the acid agglomerate, as measured by sieve analysis, is from 0.2 mm to 2 mm.

* * * * *